(12) United States Patent
Kobayashi et al.

(10) Patent No.: US 7,521,234 B2
(45) Date of Patent: *Apr. 21, 2009

(54) MAMMALIAN IMMORTALIZED LIVER CELL

(76) Inventors: Naoya Kobayashi, 2033-15, Miyoshi, Okayama-shi, Okayama 703-8261 (JP); Philippe Leboulch, 1/7 9th St., Charlestown (FR); Noriaki Tanaka, 2325-1, Rokujoinnaka, Kamogata-cho, Asakuchi-gun, Okayama 719-0252 (JP); Toshiyoshi Fujiwara, 3-5-30, Higashiyama, Okayama-shi, Okayama 703-8281 (JP); Toshinori Totsugawa, 2374, Nagawa, Seto-cho, Fukuyama-shi, Hiroshima 720-0836 (JP)

( * ) Notice: Subject to any disclaimer, the term of this patent is extended or adjusted under 35 U.S.C. 154(b) by 1170 days.

This patent is subject to a terminal disclaimer.

(21) Appl. No.: 10/169,084

(22) PCT Filed: Mar. 15, 2002

(86) PCT No.: PCT/US02/06640

§ 371 (c)(1),
(2), (4) Date: Jan. 6, 2003

(87) PCT Pub. No.: WO02/074157

PCT Pub. Date: Sep. 26, 2002

(65) Prior Publication Data

US 2004/0048374 A1    Mar. 11, 2004
US 2008/0233642 A9    Sep. 25, 2008

Related U.S. Application Data

(63) Continuation-in-part of application No. 09/809,203, filed on Mar. 16, 2001, now abandoned.

(51) Int. Cl.
C12N 5/08 (2006.01)
(52) U.S. Cl. ...................... 435/370; 435/1.1
(58) Field of Classification Search ............... 435/370, 435/1.1
See application file for complete search history.

(56) References Cited

U.S. PATENT DOCUMENTS

2004/0033215 A1* 2/2004 Kobayashi et al. ....... 424/93.21

FOREIGN PATENT DOCUMENTS

| WO | WO 97/32972 | 9/1997 |
| WO | WO 00/18239 | 4/2000 |
| WO | WO 00/61617 | 10/2000 |

OTHER PUBLICATIONS

Salmon, P. et al., Reversible Immortalization of Human Primary Cells by Lentivector-Mediated Transfer of Specific Genes, *Molecular Therapy*, Oct. 2000, vol. 2, No. 4, pp. 404-414.
Gai, J. et al., Construction of a non-tumorigenic rat hepatocyte cell line for transplantation reversal of hepatocyte immortalization by site-specific excision of the SV 40 T antigen, *Journal of Hepatology*, Nov. 2000, vol. 33, pp. 701-708.
K.A. Westerman, et al; "Reversible immortalization of mammalian cells mediated by retroviral transfer and site-specific recombination"; Proc. Natl. Acad. Sci. USA; vol. 93, pp. 8971-8976; Aug. 1996; Cell Biology.
Jin Cai, et al; "Construction of a non-tumorigenic rat hepatocyte cell line for transplantation: reversal of hepatocyte immortalization by site-specific excision of the SV40 T antigen"; Journal of Hepatology 2000; 33: 701-708.
Naoya Kobayashi, et al; "Efficient Cre/loxP Site-Specific Recombination in a HepG2 Human Liver Cell Line"; Cell Transplantation, vol. 9, pp. 737-742, 2000.
J. Nakayama, "Telomerase activation by hTRT in human normal fibroblasts and hepatocellular carcinomas", *Nature Genetics*, vol. 18 (Jan. 1998) pp. 65-68.
K. Nagao, "Telomerase reverse transcriptase mRNA expression and telomerase activity in hepatocellular carcinoma", *Journal of Gastroenterology* (1999) pp. 83-87.

* cited by examiner

*Primary Examiner*—James S Ketter
(74) *Attorney, Agent, or Firm*—Kratz, Quintos & Hanson, LLP

(57) ABSTRACT

The present invention provides a mammalian immortalized liver cell obtained by transferring a cell proliferation factor gene located between a pair of site-specific recombination sequences into a mammalian liver cell.

14 Claims, 7 Drawing Sheets

MAMMALIAN IMMORTALIZED LIVER CELL

This application is a 371 national stage application of PCT/US02/06640, filed on Mar. 15, 2002, which is a continuation-in-part under 35 U.S.C. 120 of U.S. Ser. No. 09/809,203, filed on Mar. 16, 2001 now abandoned.

TECHNICAL FIELD

The present invention relates to a mammalian immortalized liver cell. In more detail, the present invention relates to the mammalian immortalized liver cell obtained by using a gene engineering procedure.

BACKGROUND ART

Liver transplantation is the only treating method which can be utilized for patients with liver-based metabolic diseases or hepatic insufficiency. However, the treatment has problems, for example, shortage of donor livers, considerable postoperative lethality accompanied with operative risk, high costs, use of immunosuppressant over a long period and the like. Recently, isolated hepatocyte transplantation or a bio-artificial liver with living hepatocytes is desired as filler until liver transplantation or regeneration of liver. Advantages of the isolated hepatocyte transplantation or the bio-artificial liver include that it is economical compared with an operation of the liver transplantation, that the risk is few, and the like. However, in the isolated hepatocyte transplantation or the bio-artificial liver, a clinical use thereof is also limited because of the shortage of donor livers.

As an alternative to the isolated hepatocyte, there includes a liver cell-line which can be proliferated in large numbers in vitro, which maintains a property of the isolated hepatocyte and further which can provide a metabolic supplement after transplantation. It is expected that an establishment of the liver cell-line enabling to proliferate in large numbers and having a high-level liver function, and a development of a bank thereof enable the transplantation of required amount of liver-cell as need arises and dissolve the shortage of donor livers.

It is known that a cell-line which maintains appropriate function for differentiation can be produced by transferring oncogenes to immortalize cells (K. A. Westerman, et al., Proc. Natl. Acad. Sci., USA., vol 93, 8971, (1996)). However, in case where the immortalizated cell-line is infused into a living body or applied to a extracorporeal assist device such as the bio-artificial liver, there is possibility that a patient is exposed to unexpected risk of malignant transformation. It is not assured that the transplanted cell is finally rejected, even though a heterozoic cell or an incompatible homologous human cell is employed. In human, a stable chimera state with the heterozoic cell and accidental engraftment of HLA incompatible homologous tumor are reported (Gartner, et al., N. Eng. J. Med. Vol. 335, 1494, (1996); K. Paradis, et al., Science, vol. 285, 1236, (1999)). Therefore, it is desired that high-safety liver cells can be easily available in large scale.

However, in the conventional culture technique, it is difficult to proliferate the high-safety liver cells in large numbers.

In view of the above problem, the present invention purpose to provide the mammalian immortalized liver cell enabling limitless proliferation and being designed specifically to finally obtain a large number of the high-safety liver cells.

DISCLOSURE OF THE INVENTION

As a result of making an intensive study in view of the above problems, the present inventors have found the followings and completed the present invention. It has been found that by transferring a cell proliferation factor gene into a mammalian liver cell, the mammalian immortalizated liver cell enabling to proliferate in large numbers is obtained.

That is to say, the present invention relates to an immortalized liver cell (or an immortalized liver cell line) obtained by transferring a cell proliferation factor gene located between a pair of site-specific recombination sequences into a mammalian liver cell in vitro.

In the immortalized liver cell, the mammalian liver cell is preferably a human liver cell, more preferably a human adult liver cell.

In the immortalized liver cell, the cell proliferation factor gene is preferably hTERT (human telomerase reverse transcriptase) gene. Further, it is preferable that the cell proliferation factor gene is transferred using a retroviral vector.

In addition, in the immortalized liver cell, a pair of site-specific recombination sequences is preferably LoxP sequence, further GFP (green fluorescence protein) gene is preferably encoded between the pair of site-specific recombination sequences.

The immortalized liver cell is preferably cultivated in serum-free medium.

Furthermore, the present invention provides an artificial liver containing the in vitro immortalized cells.

The present invention provides an agent for treating liver insufficiency, which comprises the in vitro immortalized liver cells.

The present invention provides an assay model for drug metabolism and an infection model of human hepatitis virus, which comprise the in vitro immortalized liver cells.

Furthermore, the present invention provides an in vitro immortalized liver cell obtained by transferring a cell proliferation factor gene located between a pair of site-specific recombination sequences into a mammalian liver cell, which produces a blood coagulation factor.

The present invention also provides an in vitro immortalized liver cell obtained by transferring a cell proliferation factor gene located between a pair of site-specific recombination sequences into a mammalian liver cell, which produces albumin.

Furthermore, the present invention provides an in vitro immortalized liver cell wherein a DNA sequence encoding a site-specific recombinase at the downstream of a drug-induced promoter is integrated into a chromosome.

BEST MODE FOR CARRYING OUT THE INVENTION

Figure 1:
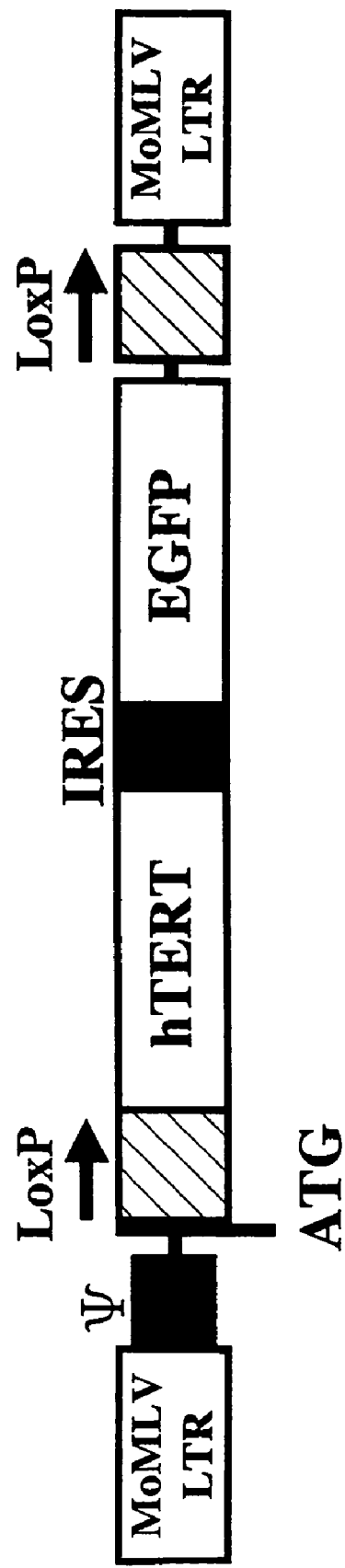
FIG. 1 shows the retroviral vector SSR#197. Herein, ATG indicates starting codon, ψ packaging signal, LoxP LoxP sequence, hTERT hTERT gene, EGFP the enhanced GFP gene, MoMLV LTR Moloney murine leukemia virus long terminal repeat, IRES encephalomyocarditis virus internal ribosome entry site, respectively.

As a mammalian liver cell employed in the present invention, there are liver cells of pig, monkey, anthropoid, human and the like. Among them, the human liver cell is preferable, the human adult liver cell is the most preferable. The human embryo liver cell may also be applied. The term "liver cell" described herein means a cell having ability to produce protein such as albumin and various blood coagulation factors which are index of liver function, ability of gluconeogenesis, ability to produce carbamide, abilities of detoxication and purification of blood, and ability to metabolize amino acid, glucide and lipid. Examples thereof include hepatocyte, liver sinusoid endothelial cell, liver stellate cell, liver Pit cell, Kupffer cell and the like.

A cell proliferation factor gene employed in the present invention is provided from normal cells and can immortalize a mammaliam liver cell by transferring. A product from the cell proliferation factor gene is those which essentially relates to cell proliferation and signal transfer in the normal cell. Examples thereof include those which function as a growth factor, which have tyrosine kinase activity in the cell membrane, which bind to GTP in the interior of the cell membrane, which have serine/threonine kinase activity in the cytoplasm, and which have ability binding to DNA in the nucleus. Such cell proliferation factor gene includes ras gene, myc gene, hTERT gene or the like. The hTERT gene is preferable, because a expression of the hTERT gene is naturally enhanced in stem and progenitor cells of organs which regenerate repeatedly over lifetime such as blood, skin, intestinal mucosa, endometrium and the like, and in lymphocytes which make clonal expansion each time they are exposed to specific antigens.

In accordance with the present invention, a retroviral vector is used for transferring the cell proliferation factor gene into the mammalian liver cell. The retroviral vector is used as means for transferring a foreign gene into an animal cell. Since the transferred gene is integrated into chromosomal DNA of the host cell, the gene is absolutely transmitted to the daughter cell, and therefore it is possible that the integrated gene is suitably expressed over long period.

As a process to transfer retroviral vectors, intravenous administration, intraperitoneal administration, intraportal administration and administration by direct puncture in case of in vivo, and a process by inoculating retroviral vectors directly on culture cells in case of in vitro are known. The intraportal administration and the administration by direct puncture and the process by direct inoculating are preferable.

As the process to transfer the retroviral vector into the culture cells by inoculating the retroviral vectors directly on the culture cells, any process can be used as long as the process achieves the object of the present invention. For example, the transferring can be performed by culturing cells which produce the retroviral vectors, and then inoculating the resulting cultural supernatant on liver cells cultured separately. Various conditions such as culture condition and seeding density about each kind of cell can be determined according to the process well known in the art.

In addition, it is preferable that the inoculation on the culture cells is only once, considering effect on the cells, for example, stability of chromosomes. However, considering a transferring efficiency of the vectors, it is preferable that the time of the inoculation on the cells is more. Based on those facts, it is the most preferable in the present invention to perform 4-hour-infection twice a day, for 3 days in total.

Furthermore, the cell proliferation factor gene used in the present invention is located between a pair of site-specific recombinant sequences so that the gene can be excised later from pro-virus transferred into a liver cell. The "site-specific recombinant sequence" is a specific base sequences recognized by a site-specific recombinase, in between the sequences a DNA-strand excision, an exchange of strands and a coupling thereof are performed.

As the site-specific recombinant sequence, there is LoxP sequence, FRT sequence or the like. Among them, LoxP sequence is preferable. The LoxP sequence is a sequence comprising 34 bases of "ATAACTTCGTATAGCATACAT-TATACGAAGTTAT" (SEQ ID No. 1) for performing a homologous recombination by Cre recombinase alone. When a pair of LoxP sequences located in the same direction presents in a same DNA molecule, a DNA sequence located therebetween is excised to become a circular molecule (excision reaction). When each of the pair of LoxP sequences is located in different DNA molecules, respectively and one of the DNA molecules is a circular DNA, the circular DNA is inserted into the other DNA molecule using the LoxP sequence (insertion reaction).

Further, in the present invention, it is necessary that a selection marker such as GFP gene presents between the pair of site-specific recombinant sequences whenever the cell proliferation factor gene is transferred into the mammalian liver cell. "Between a pair of site-specific recombinant sequences" means a position located between the pair of site-specific recombinant sequences. The GFP gene is used to identify the liver cell selectively which is infected with the retroviral vector and wherein a pro-virus is integrated into genome, by using FACS (fluorescence activated cell sorter). Therefore, if the liver cell wherein the pro-virus is integrated into genome is identified, a drug-resistance gene can be used instead of the GFP gene.

As an example of the drug-resistance gene, there is hygromycin resistance gene, neomycin resistant gene, ampicillin resistance gene, *Escherichia coli* gpt gene or the like. It is not particularly limited thereto.

"Immortalized liver cell" described herein means a cell that is not tumorigenic, has a form like a normal liver cell, keeps liver-specific function relatively and has a characteristic that it grows in a short term without any special culture condition.

Concerning cultivation of the immortalized cell, it is preferable that cell-growth rate is fast. But it is more preferable that a special coating with collagen and the like on a surface of a culture vessel is not necessary, because it is easy to handle the vessel. A doubling time of the immortalized cell is from 24 to 72 hours, preferably from 24 to 48 hours, more preferably from 24 to 36 hours. Serum-free medium, which is supplemented with no serum derived from an animal such as calf, is preferable for culture medium so that xenozoonosis is prevented. Serum-free medium is preferable for immortalized cells functionally to increase the production of albumin. CS-C medium is more preferable. CS-C medium doubling- or trebling-diluted with Dulbecco's modified Eagle medium (DMEM) may be used.

The immortalized liver cell of the present invention is a reversible immortalized cell which can be removed the transferred cell proliferation factor gene therefrom using the site-specific recombinase. The site-specific recombinase is an enzyme which recognizes the site-specific recombinant sequence specifically and performs a homologous recombination comprising an excision and coupling, independently. As the site-specific recombinase, there includes Cre recombinase, FLP recombinase or the like. Among them, the Cre recombinase is preferable. The Cre recombinase is an enzyme which recognizes the LoxP sequence specifically.

The site-specific recombinase can be encoded by an expression vector such as an adenovirus vector or a plasmid vector. Alternatively, the site-specific recombinase may be fused with TAT protein derived from human immunodeficiency virus type 1 (Green, M. and Loewenstein, P. M., Cell 55, p 179-1188, 1988: Frankel, A. D. and Pabo, C. O., Cell 55, p 1189-1193, 1988: Nagahara, H. et al., Nat. Med. 1988, 4, 1449-1452). A site-specific recombination reaction is caused in immortalized cells of the present invention by adding the fused protein to the culture medium, because TAT protein contains a protein transduction domain. Adenovirus vectors are cytotoxic. On purpose to prevent such risk, the site-specific recombinase is preferred either to be encoded by an expression vector other than an adenovirus vector or to be fused TAT protein.

The expression vector used in the present invention is not specifically limited, as long as they contain a sequence encoding the site-specific recombinase. As a promoter for the site-specific recombinase, a drug-induced promoter is preferred. The "drug-induced promoter" herein means a promoter which induces a gene expression by addition of drug. If established is an immortalized liver cell line wherein an expression vector containing both the drug-induced promoter and the site-specific recombinase is integrated into a chromosome, it is not necessary to consider infecting efficiency of virus. If such cell line is used, it is possible to optionally set up the time of the expression of the site-specific recombinase.

The drug-induced promoter is not limited specifically, and well-known promoters such as a tetracyclin induced promoter, a tamoxifen induced promoter and the like can be used. These drug-induced promoters can be selected properly by a person skilled in the art.

Therefore, the immortalized cell of the invention is preferred to be an immortalized cell wherein in addition to a sequence of TERT gene, a DNA sequence encoding a site-specific recombinase at the downstream of a drug-induced promoter is integrated into a chromosome.

Immortalized liver cells according to the present invention can be used as an assay model for drug metabolism in human liver. Between human and other animals, different are metabolic pathways of a toxic substance and a carcinogen which cause problems about effect on human body at the time of environmental pollution or the time of use thereof. Toxicity and carcinogenicity of a chemical substance including a drug, and an assay of the metabolic pathway in a body has been examined using laboratory animal such as rat, dog or hog. However, since the difference in the metabolic pathway of the chemical substance between human and laboratory animals is obvious, circumspection is required in order to apply the data of laboratory animals to human. Further, from the standpoint of the latest Animal Prevention, it is an important object to develop a means of research wherein experiments using animals are restrained as many times as possible and the change of human condition is studied using human. The immortalized liver cell according to the present invention expresses high degree of liver function, and has a great significance as a new assay model for drug metabolism which is not a substitute for laboratory animals but is closer to functions of human liver. Concretely, it is used for 1) analyzing a metabolic system of a drug in a liver, 2) studying interaction of drugs and 3) an assay of production of a mutagenic substance derived from a drug in a liver.

In addition, immortalized liver cells according to the present invention can be used for drug manufacturing. Mass production of a bioactive substance can be performed by cultivating a human-derived immortalized liver cell line on a large scale. These products include less impurity which are more difficult to remove than the bioactive substance produced by yeast, *Escherichia coli* or clone animals using gene manipulation, therefore, the product can be easily isolated. An application for drug manufacturing includes production of various kinds of blood coagulation factor, albumin and/or the like.

Furthermore, immortalized liver cells according to the present invention can be used as an infection model of human hepatitis virus. The whole picture of both human B type hepatitis virus (HBV) and human C type hepatitis virus (HCV) is becoming clear, but the viruses themselves are not confirmed yet. This is because in vitro culture system is not established yet, which can be a big barrier for fundamental researches such as clarifications of mechanisms of biology and carcinogenesis, for example, replication, particle formation and mutation of virus. It is possible to establish an infective experiment system of HBV and HCV using immortalized liver cells according to the present invention, and then to build a fundamental experiment system for formulating a mechanism of infection, and a strategy for prevention and treatment.

A treating agent for hepatic insufficiency in present invention comprises a liver cell obtained by transferring a cell proliferation factor gene into a mammalian liver cell. The treating agent for hepatic insufficiency may include other electrolyte, amino acid and glucide in order to protect the liver cell. As "hepatic insufficiency" in the present invention, there include liver failure such as acute liver failure depending on virus, drug and intoxication (for example, toadstool and the like); liver-based metabolic diseases such as hemophilia, α1-antitrypsin deficiency, galactosemia, hepatorenal tyrosinemia, maple syrup urine disease, glycogenosis type 1a, hepatic porphyria, hypobetalipoproteinemia, hypercholesterolemia, primary hyperoxaluria type 1, Crigler-Najjar syndrome type 1, hyperphenylalaninemia; acute on chronic hepatic insufficiency and the like. A treating agent of the present invention is preferred to be used for treatments of liver failure and liver-based metabolic diseases.

The dose route of the treating agent in the present invention is preferably intraportal injection, intrasplenic arterial injection or intraperitoneal transplantation. The intraportal injection and the intrasplenic arterial injection are more preferable, the intraportal injection is most preferable. The dosage of the treating agent is at least $1 \times 10^{10}$ cells, preferably $1.5 \times 10^{10}$ cells, more preferably $2.0 \times 10^{10}$ cells.

An artificial liver according to the present invention comprises immortalized liver cells obtained by transferring a cell proliferation factor gene into a mammalian liver cell and then increasing the resulting immortalized cell. "Artificial liver" herein is defined as a extracorporeal liver assist device enabling reproduction of precise liver function, wherein an aggregate of functional immortalized liver cells based on microporous glucomicrocarrier or other biocompatible supporting matrix such as capillary or ceramics regenerates glucose and urea, sets amino acid disorder in a patient to right together with rapidly neutralization of ammonia and the like being causative agent of hepatic encephalopathy.

In the artificial liver, immortalized hepatocytes expressing at least CYP3A4 and CYP2C9 are used preferably. CYP3A4 and CYP2C9 are metabolic enzymes for agent and they are also cytochrome P450-associated enzymes. According to the present invention, it was found for the first time that CYP3A4 and CYP2C9 expressions by immortalized hepatocytes are enhanced by co-cultivation with immortalized liver stellate cells. Therefore, when an artificial liver is prepared, it is preferred that immortalized liver stellate cells are used together with immortalized hepatocytes. As an immortalized cell line of hepatocytes to be used, TTNT-1 (International Patent Organism Depository of National Institute of Advanced Industrial Science and Technology, FERM BP-7498) is preferred in particular. As an immortalized liver stellate cell line to be used, TWNT-1 (International Patent Organism Depository of National Institute of Advanced Industrial Science and Technology, FERM BP-7843) is preferred in particular. The immortalized liver stellate cell line TWNT-1 does not express CYP3A4 and CYP2C9. However, TWNT-1 can enhance CYP3A4 and CYP2C9 expressed by immortalized hepatocytes when co-cultivated with immortalized hepatocytes. The ratio of immortalized hepatocytes to immortalized liver stellate is preferably 10:1 to 1:1, more preferably 10:1 to 5:1. In particular, it is the most preferred that the used ratio of immortalized hepatocytes to immortalized liver stellate is 9:1, because the ratio of immortalized hepatocytes to immortalized liver stellate is 9:1 in a living body.

An artificial liver according to the present invention may include microcarrier. Microcarrier is useful for increasing the account of cultured immortalized liver cells per unit area as substrate for immortalized liver cells. The microcarrier is preferably spherical dextran, porous resin or collagen microsphere.

In addition, high biocompatible cellulose bead is preferable, and a cellulose bead whereon a cell adhesion peptide is attached is more preferable. As the cell adhesion peptide, there include amino acid sequence such as GRGDS (SEQ ID No. 16) and RGDS (SEQ ID No. 17) (G: glycine, R: arginine, D: aspartic acid, S: serine), but it is not particularly limited thereto as long as it contains amino acid sequence RGD.

Among the collagen microsphere, a collagen microsphere consisting of only fibrin made of collagen is most preferable, because it can make the culture environment similar to in vivo.

In the present invention, the cellulose bead whereon a cell adhesion peptide is attached, and the collagen microsphere consisting of only fibrin made of collagen are preferable from the viewpoint of an occupied rate by immortalized liver cells. The collagen microsphere consisting of only fibrin made of collagen can be prepared by treating bovin dermis with pepsin to make it soluble, purifying and then forming the resultant into beads. In case of the cellulose bead whereon a cell adhesion peptide is attached, the occupied rate by deposited immortalized liver cells is in 80 to 90%, and in case of the collagen microsphere consisting of only fibrin made of collagen, the occupied rate by deposited immortalized liver cells is in about 100%. Therefore, the collagen microsphere consisting of only fibrin made of collagen is most preferable (see FIG. 4(a) and FIG. 4(b)).

The artificial liver according to the present invention may comprise a vessel in order to store the above immortalized liver cells. As a vessel, there include a hollow fiber type, a laminated type wherein cultured-immortalized liver cells are piled in a module as sort of flat plate, and a type packed with nonwoven fabric, but it is not particularly limited thereto as long as it enables high cell density and functionally maintenance of cultivation for a long term.

The artificial liver according to the present invention may have further a conduit. A portion of plasma containing noxious substrates is separated from the blood derived from a patient through the conduit by plasma separating device. The separated plasma is transferred to circuit of bio-artificial liver module side through the conduit, and in the bio-artificial liver module the noxious substrates is detoxified and glucose and the others are regenerated. The conduit may be also used in order to lead the treated plasma to the patient body. The conduit may be used to connect in series with gas exchange device, activated carbon column and the like in order to supply oxygen to cultured-immortalized liver cell in the bio-artificial liver module. The bio-artificial liver module is not particularly limited as long as it has inflow route of plasma from a patient and outflow route such that the treated plasma is lead to the patient.

The present invention is further explained in details based on the examples concretely, but is not limited thereto.

PREPARATION EXAMPLE 1

Preparation of Retroviral Vector SSR#197

Retroviral vector SSR#197 (see FIG. 1) was prepared according to the conventional method (K. A. Westerman, et al., Proc. Natl. Acad. Sci., USA., vol 93, 8971, (1996)). Concretely, the process is as follows.

1. LXSN retroviral vector was digested with EcoRI and Rsr2. After mutating the EcoRI derived the backbone vector, a polylinker comprising restriction sites (Not1, BamH1, Hind3, EcoR1, Hpa1, Sal1, Sfi1, Cla1 and Rsr2) was inserted into the resultant. Into the Not1/Hind3 site of the resulting vector, a synthesized 511LoxP sequence was inserted. hTERT gene was inserted into the EcoR1/Sal1 site.

2. A cassette vector comprising IRES-GFP, 511LoxP sequence and hepatitis B posttranscriptional regulatory element (T. S. Yen, Mol Cell Biol., 1995) was prepared as follows.

pUC19 was digested with EcoR1 and Hind3. After mutating the EcoR1 derived the backbone vector, a polylinker comprising restriction sites (Xho1, Sal1, EcoRV, Not1, Hpa1, Hind3, EcoR1, Cla1, Sfi1 and Hind3) was inserted into the resultant. Into the Not1 and Hind3 site of the resulting vector, a synthesized 511LoxP sequence was inserted. And then, prepared was a fragment wherein IRES derived from pCITE-Novagen (available from Novagen) and EGFP gene (available from Clontech Inc) were joined at the Nco1 site and the one terminus was a Sal1 site and the other terminus was a blunted Cla1 site. The fragment was inserted into the Sal1 and blunted Bgl2 site of the backbone vector.

3. SSR# 197 vector was completed by inserting the Xho1-and-Cla1 fragment derived from the cassette vector prepared in the above step 2 into the Sal1-and-Cla1 site of the vector prepared in the above step 1.

EXAMPLE 1

Establishment of Human Adult Immortalized Hepatocyte Line TTNT-1

Crip cells producing retroviral vector SSR#197 (the capacity of the Crip cell to produce retroviral vector SSR#197, i.e. titer, was $1\times10^5$ cfu/ml) were seeded in a flask T-75 at $1\times10^5$ cells/cm$^2$ and then cultured in 15 ml of DMEM+10% NCS (newborn calf serum) medium. When the cell density was about 90%, the medium was exchanged for 10 ml of DMEM+10% NCS medium.

Twenty-four hours after the medium was exchanged, 12 μg/ml of polybrene (available from Sigma) was added to a solution obtained by filtering 2 ml of cultural supernatant of the Crip cells containing retroviral vectors SSR#197 with a 0.45 μm filter. The resulting solution was added in exchange for a medium in which $1\times10^5$ cells of primary human adult hepatocytes (catalogue number CS-ABI-3716, available from Dainippon Pharmaceutical Co., Ltd) had been cultured, to infect the hepatocytes for 4 hours. The same infecting procedure was performed twice a day for 3 days in total. After the last infection in each day, the medium was exchanged for flesh CS-C medium and then hepatocytes were cultured therein.

Figure 2A:
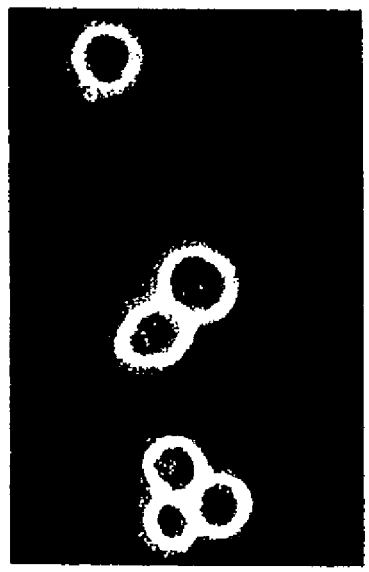
FIG. 2(a) is a phase-contrast microscopic image of hepatocytes infected with retroviral vector SSR#197.
Figure 2B:
FIG. 2(b) is a fluorescence-microscopic image of the cells shown in FIG. 2(a).

Two days after the final infection, the cells were treated with trypsin and collected. GFP-positive cells were then collected using FACS Calibur (made by Becton Dickinson) (See FIG. 2(a) and FIG. 2(b)). TTNT-1 cells was established by the limiting dilution method (seeding cells at a half cell/well) using CS-C serum free medium kit (catalogue number CS-SF-4ZO-500, available from Dainippon Pharmaceutical Co., Ltd). The TTNT-1 cell line was deposited (FERM BP-7498). The TTNT-1 cells were immortalized without a crisis of cease of cell proliferation, grew in one layer in CS-C medium, and then the number doubled for about 24 hours. The TTNT-1 cells showed morphological features of cells having a large nucleus with some nucleoli and rich intracellular granules like a parenchyma cell of a liver.

EXAMPLE 2

Expression of Gene in Human Adult Immortalized Liver Cell Line

By the RT-PCR method, in the TTNT-1 cells, the expression of genes which were important to metabolism in a liver, i.e. bilirubin-UGT gene, CYP3A4 gene, GK gene, GS gene, GST-π gene and human β-actin gene, and hTERT gene were assayed.

In the RT-PCR method, RNA was extracted from TTNT-1 cells using RNAzol (available from Cinna/Bio Tecx, Friendswood, Tex., USA) and 2 μg of the resulting total RNA was reverse-transcribed with RNA reverse transcriptase at 22° C. for 10 minutes and then at 42° C. for 20 minutes.

The obtained 2 μg of the reverse transcribed products was applied to PCR amplification using 20 μmol/ml of each primer and AmpliTaq Gold kit (available from Applied Biosystems, CA, USA) according to the protocol. PCR was performed as follows: incubation at 95° C. for 10 minutes, 35 cycles of incubation consisting of 95° C. for 30 seconds, 60° C. for 30 seconds and 72° C. for 30 seconds, and final incubation at 72° C. for 7 minutes. As primer for each gene, the following primers were used.

bilirubin-UGT gene
5' primer: ATGACCCGTGCCTTTATCAC (SEQ ID No. 2)
3' primer: TCTTGGATTTGTGGGCTTTC (SEQ ID No. 3)
CYP3A4 gene
5' primer: CCAAGCTATGCTCTTCACCG (SEQ ID No. 4)
3' primer: TCAGGCTCCACTTACGGTGC (SEQ ID No. 5)
GK gene
5' primer: ATCAAACGGAGAGGGGACTT (SEQ ID No. 6)
3' primer: AGCGTGCTCAGGATGTTGTA (SEQ ID No. 7)
GS gene
5' primer: ATGCTGGAGTCAAGATTGCG (SEQ ID No. 8)
3' primer: TCATTGAGAAGACACGTGCG (SEQ ID No. 9)
GST-π gene
5' primer: GCCCTACACCGTGGTCTATT (SEQ ID No. 10)
3' primer: GGCTAGGACCTCATGGATCA (SEQ ID No. 11)
hTERT gene
5' primer: CTGACCAGGGTCCTATTCCA (SEQ ID No. 12)
3' primer: TGGTTATCCCAAGCAAGAGG (SEQ ID No. 13)
humanβ-actin gene
5' primer: TGACGGGGTCACCCACACTGTGCCCATCTA (SEQ ID No. 14)
3' primer: CTAGAAGCATTTGCGGTGGACGATGGAGGG (SEQ ID No. 15)

Figure 3:
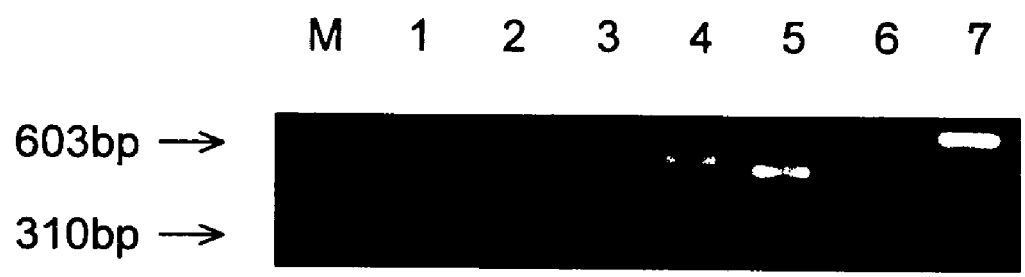
FIG. 3 shows the expression of liver specific genes and hTERT gene in TTNT-1 cell. Lanes 1 to 7 indicate an expressions of liver bilirubin-uridine phosphate glucuronocyl transferase (refer to bilirubin-UGT hereinafter) gene, cytochrome P 450 3A4 (refer to CYP3A4 hereinafter) gene, glucokinase (refer to GK hereinafter) gene, glutamine synthetase (refer to GS hereinafter) gene, glutathione-S-transferase π (refer to GST-π) gene, hTERT gene and human β-actin gene, respectively. M indicates marker.

It was shown that every one of the above genes expressed in the TTNT-1 cells (see FIG. 3).

EXAMPLE 3

Establishment of Human Adult Immortalized Liver Stellate Cell Line

TWNT-1

TWNT-1 was established in the same way as EXAMPLE 1 except that $1\times10^6$ cells of human adult liver stellate cell line LI90 was used instead of $1\times10^6$ cells of primary human adult hepatocytes (catalogue number CS-ABI-3716, available from Dainippon Pharmaceutical Co., Ltd). The LI90 was provided to everybody by Dr. Matsuura, 3-19-18, Nishishinbashi, Minato-ku, Tokyo-to, Japan. The TWNT-1 cell line was deposited (FERM BP-7843). The TWNT-1 cells showed morphological features of a liver stellate cell which has a spindle shape and contains fat droplets therein.

EXAMPLE 4

Adhesion of TTNT-1 Cells to Microcarriers $1\times10^7$ cells of TTNT-1 cells were seeded in a spinner flask with a capacity of 50 ml (catalogue number 1967-00050, available from BELLCO GLASS, Inc.) to cultivate in 25 ml of CS-C medium. In the cultivation, gyratory cultivatin was carried out for 24 hours using a 4 position Magnetic Stirrer (model 1104S, made by WAKENYAKU CO., LTD) in $CO_2$ incubator (Series 5300, made by WAKENYAKU CO., LTD) adjusted to 95% oxygen, 5% carbon dioxide and 37° C.

Figure 4A:
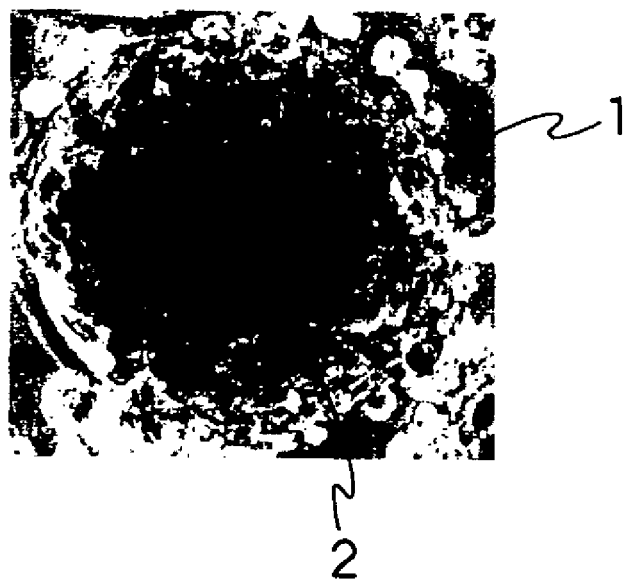
FIG. 4(a) is a microscopic image of immortalized liver cells adhering to collagen microspheres consisting of only collagen fibrin.
Figure 4B:
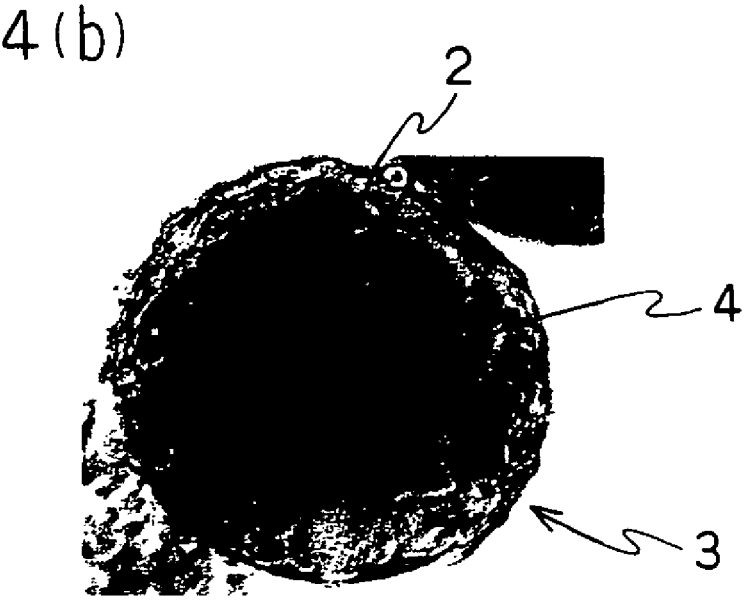
FIG. 4(b) is a microscopic image of immortalized liver cells adhering to cellulose beads whose surfaces are attached with cell adhesion peptide.

FIG. 4(a) is a microscopic image of immortalized liver cells adhering to collagen microsphere consisting of only fibrin made of collagen (commercial number KO-0000-01, available from Funakoshi Co., Ltd.). In FIG. 4(a), it is recognized that collagen microsphere 1 consisting of only fibrin made of collagen is completely covered with immortalized liver cell 2. FIG. 4(b) is a microscopic image of immortalized liver cells adhering to the cellulose bead whereon cell adhesion peptides were attached (made by Kuraray Co., Ltd.). In FIG. 4 (b), it is observed that the cellulose bead 3 whereon cell adhesion peptides were attached is covered with immortalized liver cell 2 in lower occupied rate than (a), and that there is surface 4 of bead without adhering cells.

EXAMPLE 5

Test for Tumorigenesis

Figure 5:
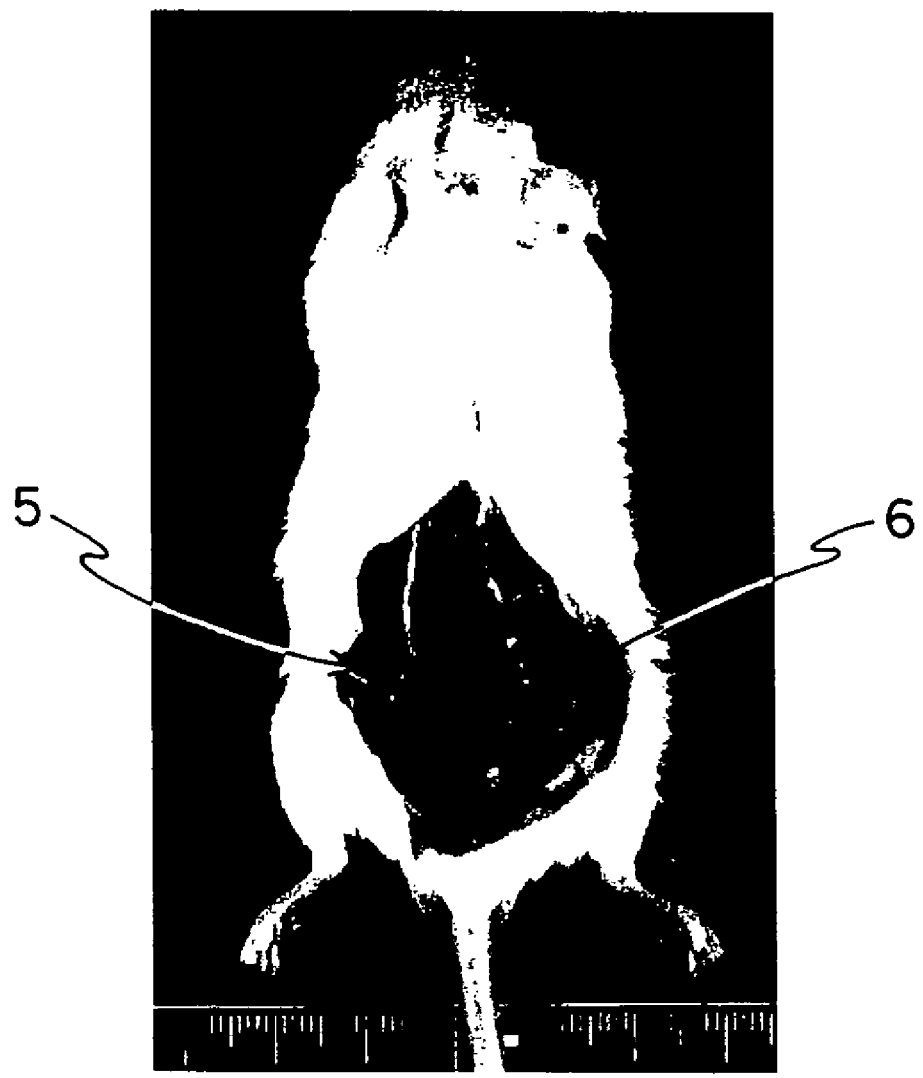
FIG. 5 shows a mouse one month after the transplantation of both TTNT-1 cells and PLC/PRF/5 cells

Subcutaneously, $1 \times 10^7$ cells of TTNT-1 were transplanted to mouse with severe combined immunodeficiency (SCID). As a positive control, $1 \times 10^6$ cells of PLC/PRF/5 cell line derived from human hepatoma were subcutaneously transplanted to the same mouse. The PLC/PRF/5 was provided to everybody by Institute of Development, Aging and Cancer, Tohoku University (4-1, Seiryo-cho, Aoba-ku, Sendai-shi, Miyagi-ken, Japan). As a result, TTNT-1 did not form any tumor a month after the transplantation (arrow 5 in FIG. 5). On the other hand, a tumor was observed macroscopically a week after the transplantation, and then about 3 cm size of tumor was observed a month after the transplantation (arrow 6 in FIG. 5). Therefore, it was shown that TTNT-1 was extremely safe.

EXAMPLE 6

Co-cultivation of TTNT-1 and TWNT-1

Mixed were $1.8 \times 10^6$ cells of TTNT-1 and $0.2 \times 10^6$ cells of TWNT-1, and the mixture cells were seeded in a petri dish having a diameter of 10 cm and then cultivated in 10 ml of CS-C medium. The cultivation was carried out for a week in $CO_2$ incubator (Series 5300, made by WAKENYAKU CO., LTD) adjusted to 95% oxygen, 5% carbon dioxide and 37° C. As a control, $1.8 \times 10^6$ cells of TTNT-1 alone was cultivated in the same way.

Figure 6:
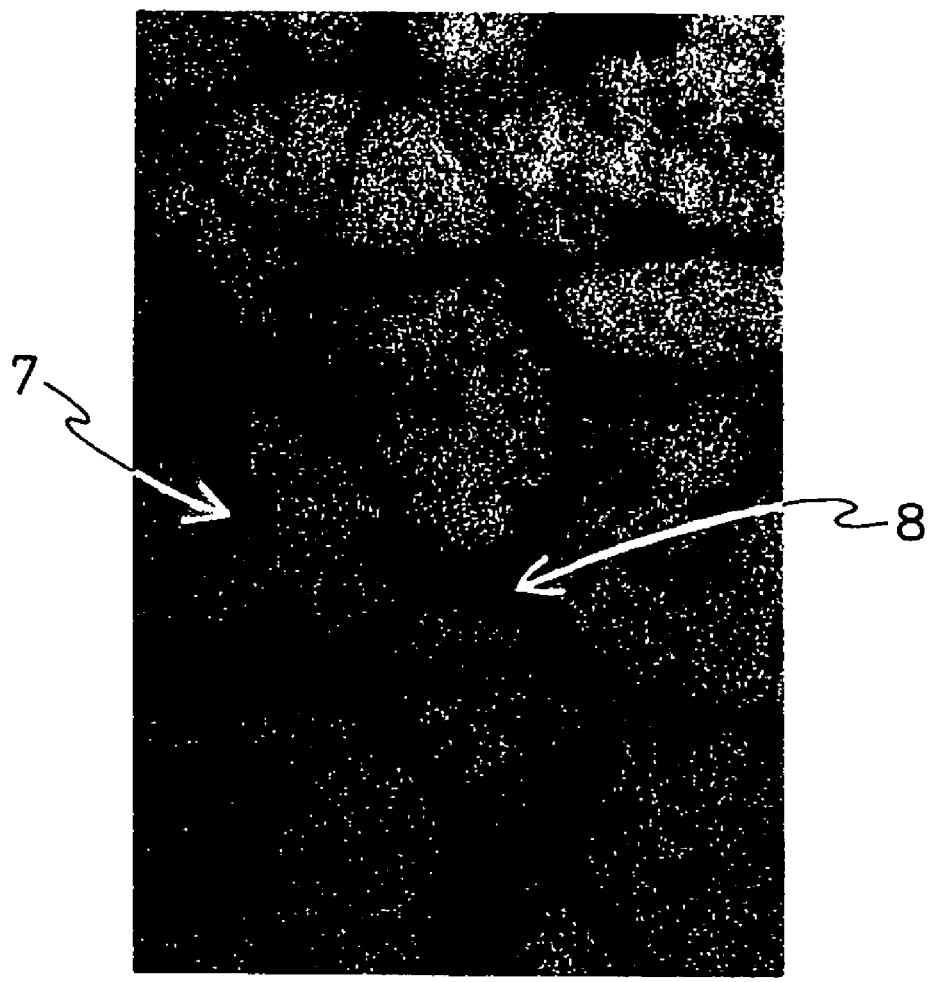
FIG. 6 shows a phase-contrast microscopic image of a hepatic lobule-like structure observed after TTNT-1 and TWNT-1 cells were co-cultured for a week.

As a result of the co-cultivation, hepatic lobule-like structure was observed. A phase-contrast microscopic image of a hepatic lobule-like structure observed after TTNT-1 and TWNT-1 cells were co-cultured for a week. A phase-contrast microscopic image of a hepatic lobule-like structure observed a week after co-cultivation of TTNT-1 and TWNT-1 cells. In FIG. 6, arrow 7 shows TTNT-1 and arrow 8 shows TWNT-1.

Figure 7A:
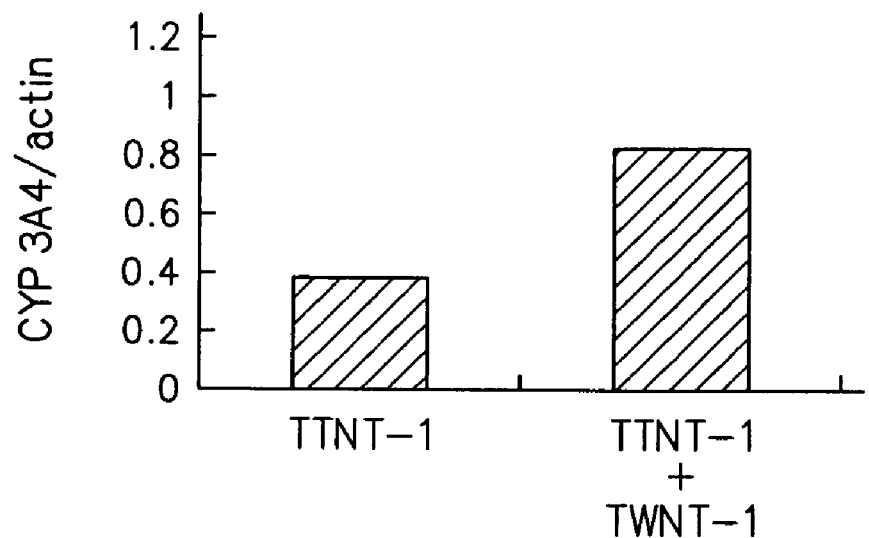
FIG. 7(a) is a graph showing the ratio of CYP3A4 to actin which were detected by western blotting.
Figure 7B:
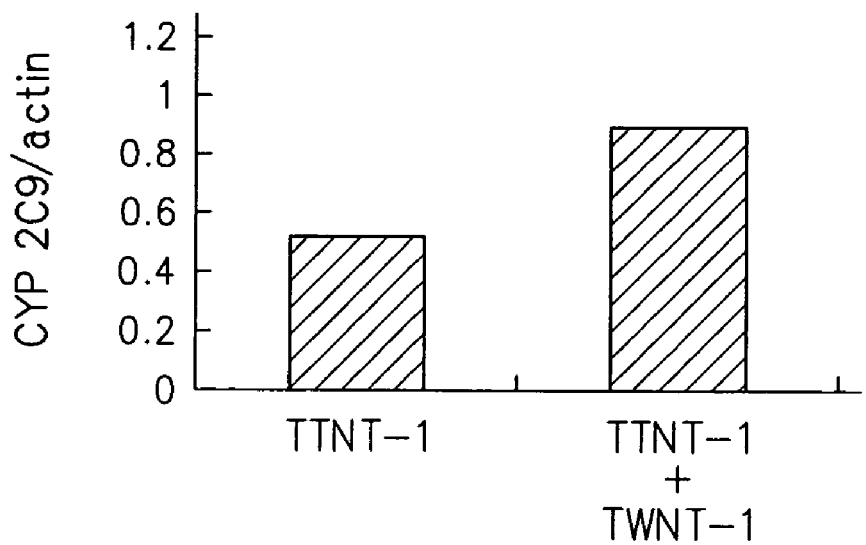
FIG. 7(b) is a graph showing the ratio of CYP2C9 to actin which were detected by western blotting.

Next, cultured cells were rinsed with PBS (Phosphate Buffered saline) on ice, collected with a scraper, and then precipitated by centrifugation (3000 rpm, 3 minutes). The supernatant was removed. To the resulting pellet, about 3-fold volume of cell lytic solution (150 mM NaCl, 5 mM EDTA, 1% Triton X-100, 1 mM DTT, 10 μg/ml leupeptin, 10 μg/ml aprotinin, 200 μg/ml phenylmethanesulfonyl fluoride, 10 mM Tris, pH 7.3) was then added. The resulting mixture was mixed by pipetting and then the resulting suspension was allowed to stand on ice for 10 minutes. The supernatant of the suspension was collected by centrifuging (15000 rpm, 20 minutes) to precipitate insoluble proteins. Then, western blotting was carried out according to a general method by using 30 μg of protein contained in the supernatant. The ratio of CYP3A4 to actin detected by the western blotting was then obtained by using NIH image soft. The NIH image soft was provided on NIH home page. Furthermore, the ratio of CYP2C9 to actin detected by the western blotting was also obtained in the same way. Actin was used as an internal control. The results are shown in FIG. 7(a) and FIG. 7(b). It is shown in FIG. 7(a) that in case where TTNT-1 and TWNT-1 were co-cultivated, amount of expressed CYP3A4 was increased 1.9-fold than that of the control. It is shown in FIG. 7(b) that in case of the co-cultivation, amount of expressed CYP2C9 was increased 1.5-fold than that of the control.

INDUSTRIAL APPLICABILITY

An in vitro immortalized liver cell can be obtained by transferring a cell proliferation factor gene located between a pair of site-specific recombination sequences into a mammalian liver cell in vitro. The in vitro immortalized liver cells of the invention are useful for an artificial liver. Furthermore, the in vitro immortalized liver cells of the invention are useful for an agent for treating liver insufficiency, an assay model for drug metabolism test and an infection model of human hepatitis virus. In addition, the in vitro immortalized liver cells of the invention are used for the preparation of coagulation factors and/or albumin.

Sequence Listing Free Text

SEQ No.1: LoxP sequence
SEQ No.2: 5' primer for polymerase chain reaction to detect Bilirubin-UGT gene
SEQ No.3: 3' primer for polymerase chain reaction to detect Bilirubin-UGT gene
SEQ No.4: 5' primer for polymerase chain reaction to detect CYP3A4 gene
SEQ No.5: 3' primer for polymerase chain reaction to detect CYP3A4 gene
SEQ No.6: 5' primer for polymerase chain reaction to detect GK gene
SEQ No.7: 3' primer for polymerase chain reaction to detect GK gene
SEQ No.8: 5' primer for polymerase chain reaction to detect GS gene
SEQ No.9: 3' primer for polymerase chain reaction to detect GS gene
SEQ No.10: 5' primer for polymerase chain reaction to detect GST-π gene
SEQ No.11: 3' primer for polymerase chain reaction to detect GST-π gene
SEQ No.12: 5' primer for polymerase chain reaction to detect hTERT gene
SEQ No.13: 3' primer for polymerase chain reaction to detect hTERT gene
SEQ No.14: 5' primer for polymerase chain reaction to detect human β-actin gene
SEQ No.15: 3' primer for polymerase chain reaction to detect human β-actin gene
SEQ No.16: Cell adhesion peptide
SEQ No.17: Cell adhesion peptide

The invention claimed is:

1. An in vitro mammalian immortalized liver cell obtained by transferring hTERT gene located between a pair of site-specific recombination sequences into a mammalian liver cell.

2. The in vitro mammalian immortalized liver cell of claim 1, wherein the mammalian liver cell is a human liver cell.

3. The in vitro mammalian immortalized liver cell of claim 2, wherein the human liver cell is a human adult liver-cell.

4. The in vitro mammalian immortalized liver cell of claim 1, wherein the hTERT gene is transferred using a retrovirus vector.

5. The in vitro mammalian immortalized liver cell of claim 1, wherein the pair of site-specific recombination sequences is LoxP sequence.

6. The in vitro mammalian immortalized liver cell of claim 1, wherein GFP gene is present between the pair of site-specific recombination sequences.

7. The in vitro mammalian immortalized liver cell of claim 1, which is proliferated in serum-free medium.

8. An artificial liver containing the in vitro immortalized cells of claim 1.

9. An agent for treating liver insufficiency, which comprises the in vitro immortalized cells of claim 1.

10. An assay model for drug metabolism, which comprises the in vitro immortalized liver cells of claim 1.

11. An infection model of human hepatitis virus, which comprises the in vitro immortalized liver cells of claim 1.

12. The in vitro mammalian immortalized liver cell of claim 1, which produces a blood coagulation factor.

13. The in vitro mammalian immortalized liver cell of claim 1, which produces albumin.

14. An in vitro immortalized liver cell wherein a DNA sequence encoding a site-specific recombinase at the downstream of a drug-induced promoter is integrated into a chromosome.

* * * * *

SEQUENCE LISTING

<160> NUMBER OF SEQ ID NOS: 17

<210> SEQ ID NO 1
<211> LENGTH: 34
<212> TYPE: DNA

```
<213> ORGANISM: PI phage
<220> FEATURE:
<223> OTHER INFORMATION: LoxP sequence

<400> SEQUENCE: 1
ataacttcgt atagcataca ttatacgaag ttat                                34

<210> SEQ ID NO 2
<211> LENGTH: 20
<212> TYPE: DNA
<213> ORGANISM: Artificial Sequence
<220> FEATURE:
<223> OTHER INFORMATION: 5' primer for polymerase chain reaction to
      detect Bilirubin-UGT gene

<400> SEQUENCE: 2
atgacccgtg cctttatcac                                                20

<210> SEQ ID NO 3
<211> LENGTH: 20
<212> TYPE: DNA
<213> ORGANISM: Artificial Sequence
<220> FEATURE:
<223> OTHER INFORMATION: 3' primer for polymerase chain reaction to
      detect Bilirubin-UGT gene

<400> SEQUENCE: 3
tcttggattt gtgggctttc                                                20

<210> SEQ ID NO 4
<211> LENGTH: 20
<212> TYPE: DNA
<213> ORGANISM: Artificial Sequence
<220> FEATURE:
<223> OTHER INFORMATION: 5' primer for polymerase chain reaction to
      detect CYP3A4 gene

<400> SEQUENCE: 4
ccaagctatg ctcttcaccg                                                20

<210> SEQ ID NO 5
<211> LENGTH: 20
<212> TYPE: DNA
<213> ORGANISM: Artificial Sequence
<220> FEATURE:
<223> OTHER INFORMATION: 3' primer for polymerase chain reaction to
      detect CYP3A4 gene

<400> SEQUENCE: 5
tcaggctcca cttacggtgc                                                20

<210> SEQ ID NO 6
<211> LENGTH: 20
<212> TYPE: DNA
<213> ORGANISM: Artificial Sequence
<220> FEATURE:
<223> OTHER INFORMATION: 5' primer for polymerase chain reaction to
      detect GK gene

<400> SEQUENCE: 6
atcaaacgga gaggggactt                                                20

<210> SEQ ID NO 7
<211> LENGTH: 20
<212> TYPE: DNA
<213> ORGANISM: Artificial Sequence
<220> FEATURE:
```

```
<223> OTHER INFORMATION: 3' primer for polymerase chain reaction to
      detect GK gene

<400> SEQUENCE: 7
agcgtgctca ggatgttgta                                                    20

<210> SEQ ID NO 8
<211> LENGTH: 20
<212> TYPE: DNA
<213> ORGANISM: Artificial Sequence
<220> FEATURE:
<223> OTHER INFORMATION: 5' primer for polymerase chain reaction to
      detect GS gene

<400> SEQUENCE: 8
atgctggagt caagattgcg                                                    20

<210> SEQ ID NO 9
<211> LENGTH: 20
<212> TYPE: DNA
<213> ORGANISM: Artificial Sequence
<220> FEATURE:
<223> OTHER INFORMATION: 3' primer for polymerase chain reaction to
      detect GS gene

<400> SEQUENCE: 9
tcattgagaa gacacgtgcg                                                    20

<210> SEQ ID NO 10
<211> LENGTH: 20
<212> TYPE: DNA
<213> ORGANISM: Artificial Sequence
<220> FEATURE:
<223> OTHER INFORMATION: 5' primer for polymerase chain reaction to
      detect GST-pi gene

<400> SEQUENCE: 10
gccctacacc gtggtctatt                                                    20

<210> SEQ ID NO 11
<211> LENGTH: 20
<212> TYPE: DNA
<213> ORGANISM: Artificial Sequence
<220> FEATURE:
<223> OTHER INFORMATION: 3' primer for polymerase chain reaction to
      detect GST-pi gene

<400> SEQUENCE: 11
ggctaggacc tcatggatca                                                    20

<210> SEQ ID NO 12
<211> LENGTH: 20
<212> TYPE: DNA
<213> ORGANISM: Artificial Sequence
<220> FEATURE:
<223> OTHER INFORMATION: 5' primer for polymerase chain reaction to
      detect hTERT gene

<400> SEQUENCE: 12
ctgaccaggg tcctattcca                                                    20

<210> SEQ ID NO 13
<211> LENGTH: 20
<212> TYPE: DNA
<213> ORGANISM: Artificial Sequence
<220> FEATURE:
<223> OTHER INFORMATION: 3' primer for polymerase chain reaction to
```

-continued

```
          detect hTERT gene

<400> SEQUENCE: 13
tggttatccc aagcaagagg                                               20

<210> SEQ ID NO 14
<211> LENGTH: 30
<212> TYPE: DNA
<213> ORGANISM: Artificial Sequence
<220> FEATURE:
<223> OTHER INFORMATION: 5' primer for polymerase chain reaction to
      detect human beta-actin gene

<400> SEQUENCE: 14
tgacggggtc acccacactg tgcccatcta                                    30

<210> SEQ ID NO 15
<211> LENGTH: 30
<212> TYPE: DNA
<213> ORGANISM: Artificial Sequence
<220> FEATURE:
<223> OTHER INFORMATION: 3' primer for polymerase chain reaction to
      detect human beta-actin gene

<400> SEQUENCE: 15
ctagaagcat ttgcggtgga cgatggaggg                                    30

<210> SEQ ID NO 16
<211> LENGTH: 5
<212> TYPE: PRT
<213> ORGANISM: Artificial Sequence
<220> FEATURE:
<223> OTHER INFORMATION: Cell adhesion peptide

<400> SEQUENCE: 16

Gly Arg Gly Asp Ser
1               5

<210> SEQ ID NO 17
<211> LENGTH: 4
<212> TYPE: PRT
<213> ORGANISM: Artificial Sequence
<220> FEATURE:
<223> OTHER INFORMATION: Cell adhesion peptide

<400> SEQUENCE: 17

Arg Gly Asp Ser
1
```